United States Patent [19]

Smith

[11] Patent Number: 5,188,103
[45] Date of Patent: Feb. 23, 1993

[54] FACIAL BANDAGE WITH THERMAL TREATMENT POUCH

[76] Inventor: Veronica C. Smith, 2951 60th Ave., Oakland, Calif. 94605

[21] Appl. No.: 736,861

[22] Filed: Jul. 29, 1991

Related U.S. Application Data

[63] Continuation-in-part of Ser. No. 597,883, Oct. 12, 1990, abandoned.

[51] Int. Cl.$^5$ .............................................. A61F 7/00
[52] U.S. Cl. ..................................... 128/380; 128/402
[58] Field of Search ............................... 128/399–403, 128/379, 384, 380; 62/530, 259.3

[56] References Cited

U.S. PATENT DOCUMENTS

| | | | |
|---|---|---|---|
| 2,071,706 | 2/1937 | Reach | 128/380 |
| 4,190,054 | 2/1980 | Brenam | 128/402 |
| 4,586,506 | 5/1986 | Nangle | 128/403 |
| 4,805,620 | 2/1989 | Meistrell | 128/402 |
| 5,016,629 | 5/1991 | Kanare | 128/402 |
| 5,020,536 | 6/1991 | Keen | 128/402 |

FOREIGN PATENT DOCUMENTS 2071 6/1984 PCT Int'l Appl. ................. 128/402

*Primary Examiner*—Mark Graham
*Attorney, Agent, or Firm*—Owen, Wickersham & Erickson

[57] ABSTRACT

An adjustable facial dressing for compression and/or support of and thermal treatment of facial features for medical treatment is disclosed. A main band elastic can be positioned on the face (head or neck) in various positions by adjusting the position of an integral hook tape tab at any position along the main band. A thermal treatment assembly having a pouch containing a thermal reservoir is removably engageable with the band at any position, such that temperature treatment is effectively provided to any part of a face. A separate anchor strap has hook tape tabs at its ends. The hook tape tabs each engage one of two generally opposite sides of the main band around only one side of the face (head or neck). The anchor strap hook tape tabs can engage the main band at any position along the main band, to thereby provide compression or support of the face/head/neck area covered and assist in maintaining the position of the main band on the face. More than one anchor strap may be used. The plush backing of the elastic band used allows the straps to be secured anywhere on the band by the hook tabs on the end of the straps. This makes the bandage easily adjustable and adaptable to various procedures.

2 Claims, 5 Drawing Sheets

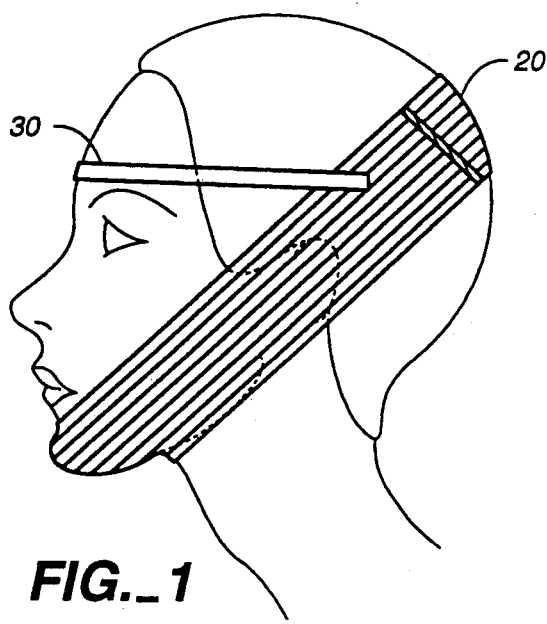
FIG._1
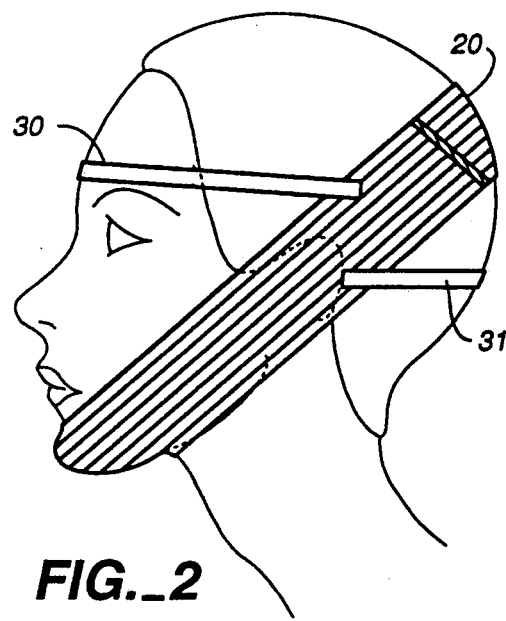
FIG._2
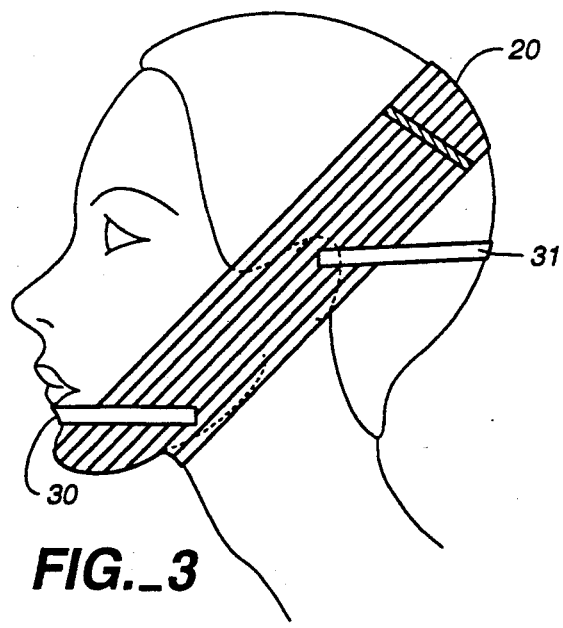
FIG._3
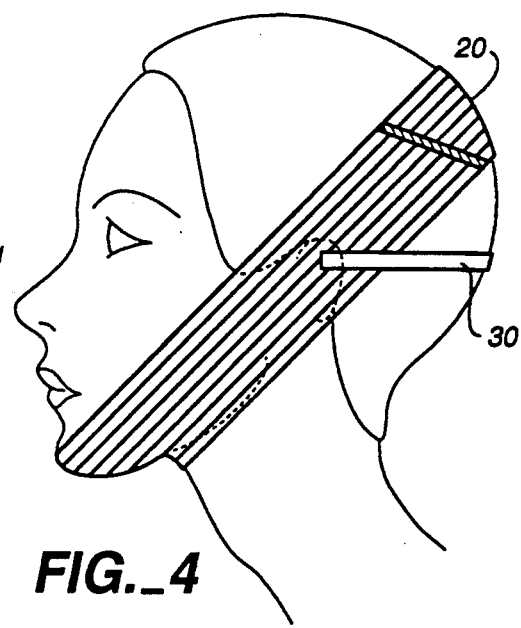
FIG._4

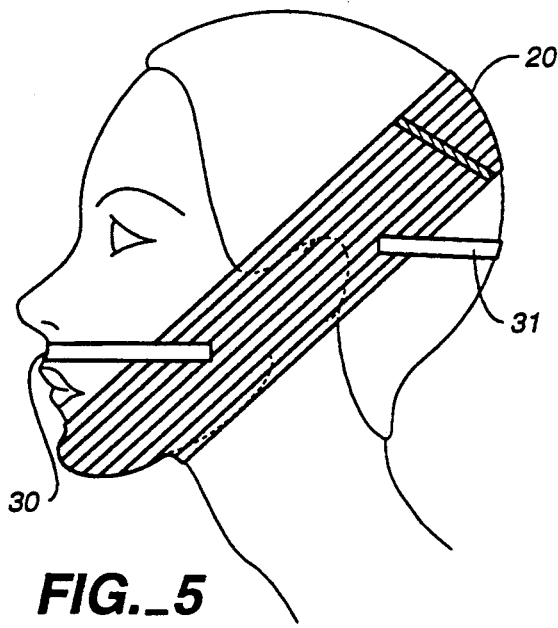
FIG._5
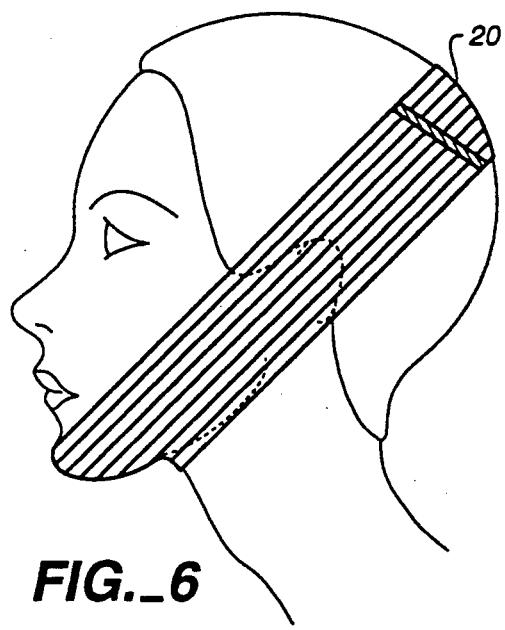
FIG._6
FIG._7
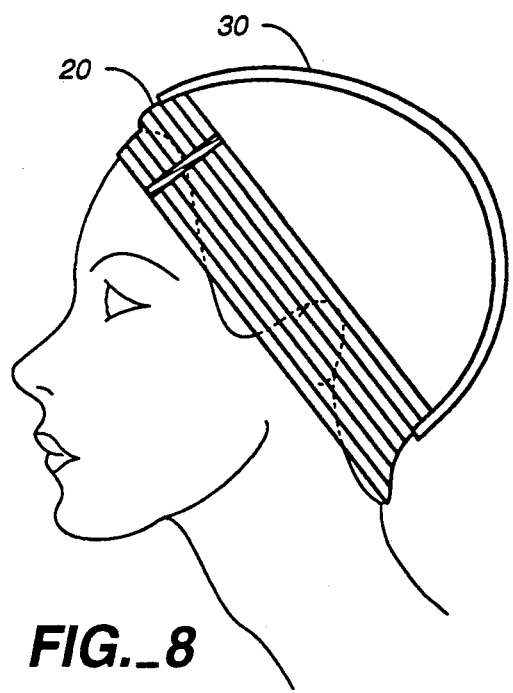
FIG._8

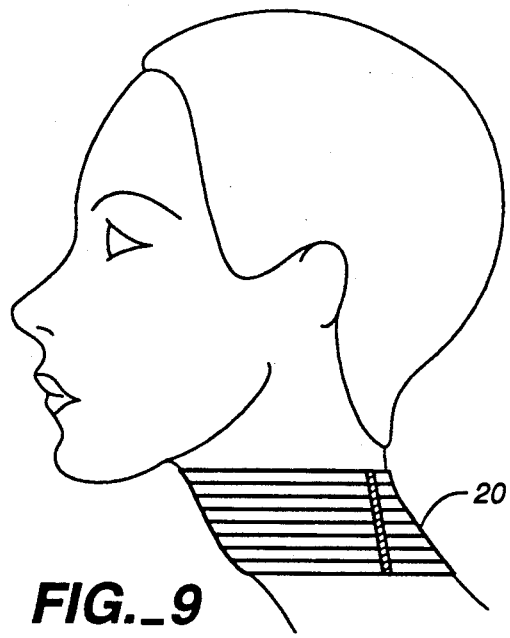
FIG._9
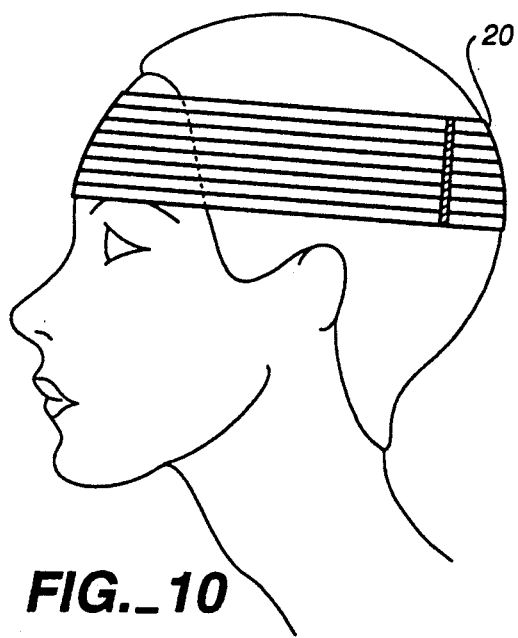
FIG._10
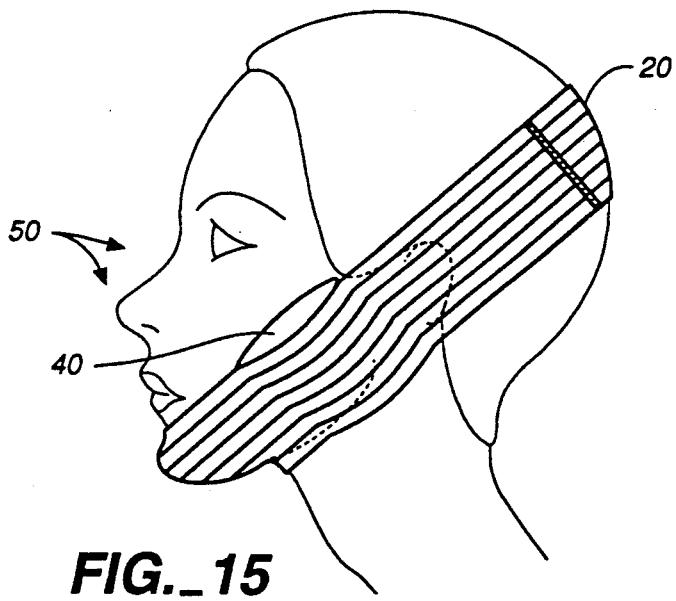
FIG._15
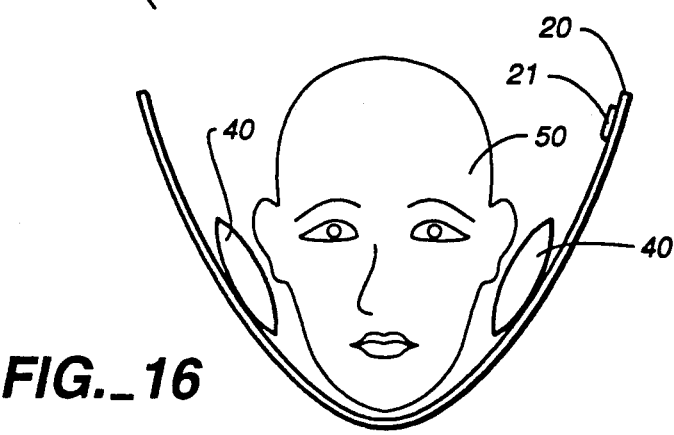
FIG._16

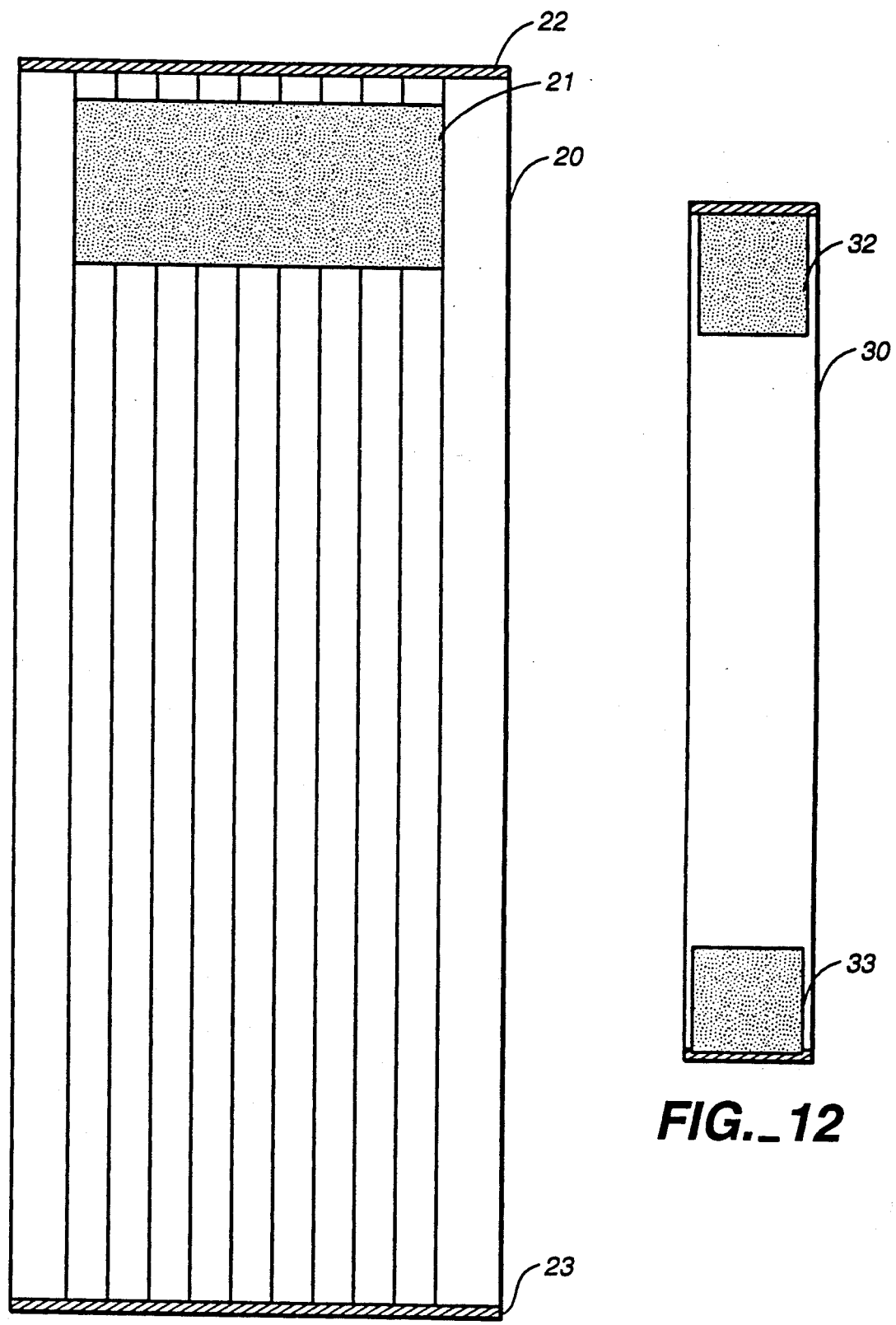
FIG._11
FIG._12

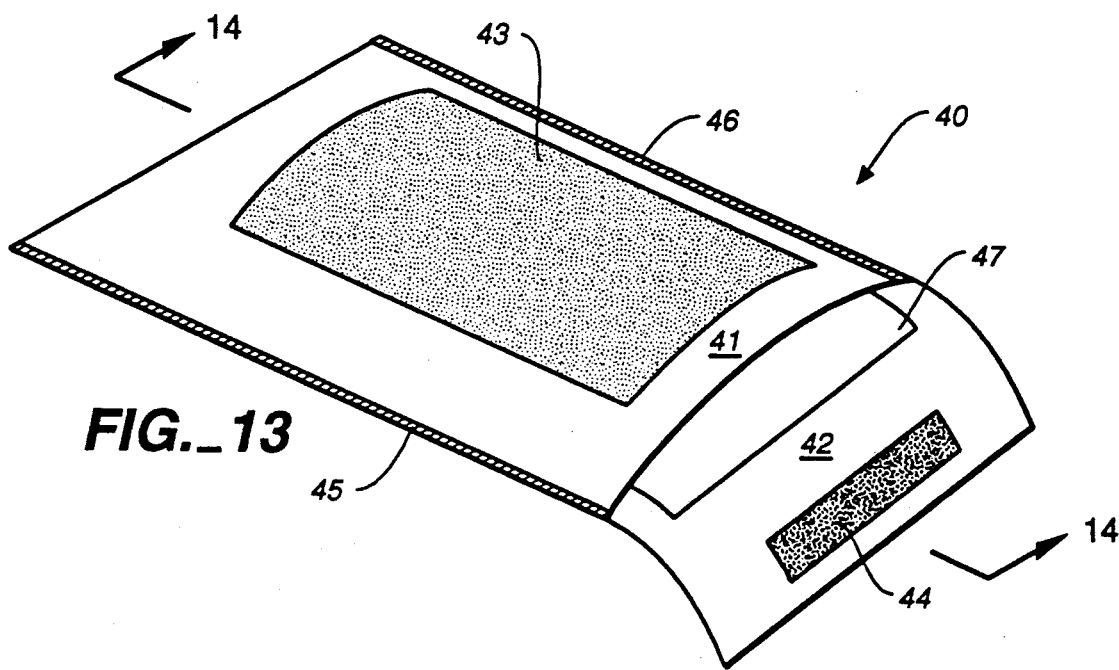
FIG._13
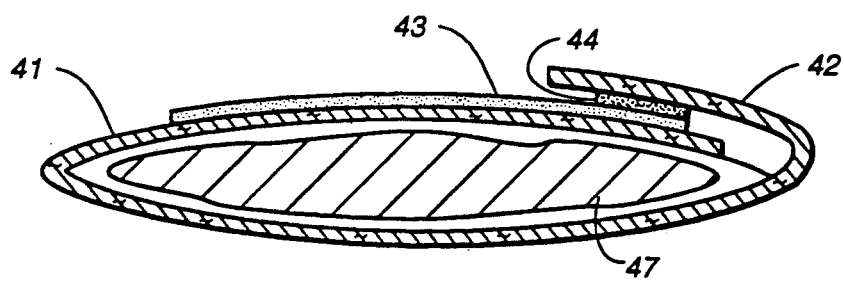
FIG._14

FACIAL BANDAGE WITH THERMAL TREATMENT POUCH

This application is a continuation-in-part of application Ser. No. 07/597,883, originally filed on Oct. 12, 1990, now abandoned and is hereby incorporated by reference herein.

FIELD OF THE INVENTION

This application relates to the field of medical garments to support thermal treatment means for the face/-head/neck.

BACKGROUND OF THE INVENTION

The neck and head are areas of the body for which there are many procedures to correct ailments or deformities that may need surgical correction and/or therapeutic compression and/or support. There may be a surgical correction or nonsurgical correction. Surgical corrections generally fall into two categories: elective surgery (cosmetic) or nonelective surgery (necessary for good mental or physical health).

Since the identification of facial (head/neck) maladies and their corrective procedures, there has been an ongoing need for a simple, contouring, adjustable, versatile as well as effective facial bandage. In the past a facial bandage that provided adequate compression and/or support; had the ability to contour the facial structure and be adjustable and adaptable enough to be used for an array of procedures has not been available. Since there are a variety of facial (head/neck) procedures that may require support and/or compression and also cold and/or hot therapy, an adaptable versatile apparatus is necessary or needed.

SUMMARY OF THE INVENTION

The invention provided an easy, effective, adjustable means to apply hot or cold therapy to a facial structure.

This invention includes a pouch to carry thermal treatment means (enclosed ice or some type of reusable ice (energy reservoir)) for cold/hot therapy which attaches to the inside of a facial bandage by a removable hook tape covering (e.g. hook part of Velcro ™) which is attached to the pouch.

A facial bandage for the pouch is easy to apply; comfortable; versatile (used for an array of procedures); easily adjustable; has the ability to contour with the facial (head/neck) structure; and has the ability to provide adequate compression and/or support to the facial (head/neck) structure.

The pouch can be easily adjusted and its position changed with respect to the facial bandage depending on the area needing therapy (e.g. jaws, under chin, other areas of the face). This leaves the patient's hands free for other activities and/or rest, as the cold/hot therapy pouches and their contents are carried (held or supported) by the facial bandage.

Another embodiment of the invention includes an adjustable facial band which compresses and supports facial structures around which it is wrapped as well as containing and supporting a pouch which contains thermal treatment means. The band can be worn in various positions on the face (head and neck) and can be assisted by one or more anchoring straps. The thermal treatment pouches with removably engageable attachment means is provided to engage the band at any location along the band.

BRIEF DESCRIPTION OF THE DRAWINGS

FIGS. 1, 4, and 8 show various positions of a band and an anchor strap as worn on a face (head and neck);

FIGS. 2, 3, and 5 show various positions of a band with two anchor straps as worn on a face (head and neck);

FIGS 6, 7, 9, and 10 show various positions of a band as worn on a face (head and neck);

FIG. 11 shows a band of an embodiment of the invention;

FIG. 12 shows an anchor strap of an embodiment of the invention;

FIG. 13 shows a perspective vie of an open pouch assembly according to an embodiment of the invention;

FIG. 14 shows a cross-sectional view of the pouch assembly of FIG. 13 when in a closed position;

FIG. 15 shows a perspective view of an embodiment of the invention as worn on a face; and FIG. 16 shows an embodiment of the invention in a front view during application of an embodiment of the invention to a face.

DETAILED DESCRIPTION

FIGS. 1-12 repeat the drawings of application Ser. No. 07/597,883 now abandoned and show various positions of a band 20 under which a pouch assembly 40 could be mounted. FIGS. 13-16 show the construction of an embodiment of a pouch assembly 40 and its interaction with a facial bandage having the band 20, the band 20 and one anchor strap 30, or the band 20 and two (or more) anchor straps 30, 31 as pictured in FIGS. 1-10.

FIGS. 13 and 14 show an embodiment of a pouch assembly 40 according to the invention. The pouch assembly 40 includes a pouch 41 having an end flap 42. The pouch 41 has attached to its side a hook tape covering 43 which covers an elongated portion of the central upper side of the pouch 41 (as pictured). The pouch 41 is constructed of a single piece of material which is looped on itself and has an overlapping flap 42 at its end. The facing folded portions of the pouch 41 are sewn together at either side by sewn stitching 45, 46. A loop (hook receiving) tape tab 44 is attached to the inside of the flap 42 such that when it is folded over the end of the pouch opening it will contact the end of the hook tape covering 43 and removably engage it to hold a thermal reservoir container (thermal treatment means) 47 in the pouch in any mounting position.

A cross-sectional view of the pouch in a closed position can be seen in FIG. 14. The hook tape covering 43 is substantially exposed except for a small area at the flap end of the hook tape covering 43 which engages the loop tape tab 44 of the flap 42. The exposed portion of the hook tape covering 43 is the means by which the thermal pouch assembly 40 engages the band 20. The pouch assembly 40 is held there by the engaged hook tape covering hooks at any position and location along the band 20.

FIG. 15 shows a thermal pouch assembly 40 being supported on a face 50 by the band 20. FIG. 15 shows only one example of how the thermal pouch assembly 40 could be engaged with the band 20 in any of a variety of various configurations of the band, other examples of which are shown in FIGS. 1-10 or in any other configuration that a person of ordinary skill in the art would understand was available for support and mounting. Therefore, the thermal pouch assembly 40 as shown in FIG. 15 can be mounted and held in position by the band 20 and/or used with one or more anchor straps 30, 31 similar to the configurations shown in FIGS. 1-10.

FIG. 16 shows two thermal pouch assemblies 40 removably engaged with the band 20 supporting the thermal pouch assemblies 40 to the face 50 before the band 20 is closed. Once it has been determined that the thermal pouch assemblies 40 have been positioned correctly, the ends of the band 20 can be overlapped so that when engaged, the hook tape tab 21 on the band 20 creates a constricting loop to support the thermal pouch assemblies 40 to the face in a position which is acceptable to the user because of the vast adjustability of the band and its supporting anchor strap(s) 30 (and/or 31).

The contents of the pouch assembly 40 includes a thermal reservoir container 47 (the "Re-Usable Cold & Hot Kompress" manufactured by Physicians & Nurses Manufacturing Corporation of Larchmont, N.Y., is suitable for this use) which is sized to fit into the pouch 41. The cotton pouch 41 acts as an insulating layer between the plastic container for the compress and the patient's skin to prevent burning or freezing of a patient's skin during the initial application of the thermal pouch assembly to the face.

The thermal pouch assembly 40 is sized to be approximately 3.5" wide and 5" long not including the flap 42 (which extends approximately 1.5"). Other pouch sizes larger or smaller as desired for treatment can be provided. The pouch is made of a material (preferably knit cotton) which is readily stretchable to conform closely to the thermal reservoir it contains and the face against which it is placed. The hook tape covering 43 is approximately 3¾" by 2" and is approximately centered on one side of the pouch 42. The loop tape tab 44 is approximately 1½" by ⅝" and is located adjacent to the end of the flap 42.

FIGS. 1-10 show several of the various positions in which a band 20 and anchor straps 30, 31 can be worn. A thermal pouch assembly can be located at any position along the band 20 as shown in any of these figures.

In FIG. 1 the band 20 is worn over the chin and over the top of the head with an anchor strap 30 across the forehead.

In FIG. 2 the band 20 is worn over the chin and over the top of the head with two anchor straps 30, 31, one across the forehead and one across back of the head.

In FIG. 3 the band 20 is worn over the chin and over the top of the head with the two anchor straps, 30, 31 one under the bottom lip and one across back of the head.

In FIG. 4 the band 30 is worn over the chin and over the top of the head with the anchor strap 30 across the back of the head.

In FIG. 5 the band 20 is worn over the chin and over the top of the head with one anchor strap 30 worn above the upper lip and the other anchor strap 31 worn across the back of head.

In FIG. 6 the band 20 is worn over the chin and over top of the head.

In FIG. 7 the band 20 is worn behind the head at the neck and across the forehead.

In FIG. 8 the band 20 is worn behind the head at the neck and across the forehead with the anchor strap 30 over the top of the head.

FIG. 9 shows the band 20 worn wrapped around the neck.

FIG. 10 shows the band 20 worn over the forehead.

FIG. 11 shows an embodiment of the band 20. It is approximately 2.5" to 4" wide and 22" to 30.5" long. Each end is overlocked with a wooly nylon thread 22,23. On one end a 2"×2" to 3"×3.5" strip of hook tape (tab) 21 is sewn down. This hook tape tab 21 attaches anywhere on the band 20 (as a closure). The band 20 is made of a mono-filament elastic of polyester, rubber, and nylon and is plush on both sides.

FIG. 12 shows an embodiment of the anchor strap 30 (or 31) which is an elastic ¾" to 3" wide with hook tapes 32,33 sewn on both ends.

FIG. 14 is a side view of a person wearing the Facial Bandage with the thermal pouch assembly 40 inserted on the side. The pouch assembly 40 is located inside the band next to the skin of the face and is anchored to the band 20 and in position by the hook tape covering 43 attached to the pouch 42. The hook tape covering 43 is removably engaged to the inside of the band 20.

Embodiments of the invention include the band 20 with one or two elastic straps 30,31 each approximately ¾" to 3" wide and 10" to 13.5" long. Both ends of each strap 30,31 are turned down about ¼" with a strip of hook tape (tab) (e.g. 32,33) ¾" to 3" long sewn down, but may also be constructed without turning the ends down. The size of the hook tape tab is varied to approximately match the size of the end of strap to which it is attached. The straps 30,31 anchor the band 20 in position and serve as support for the band. The straps 30,31 can be placed anywhere on the band 20 by the hook tape tabs (e.g. 32,33). Embodiments of the facial dressing provide alternately one or two anchor straps.

This bandage 20 is used without the use of corresponding loop tape (the complement to hook tape) to secure the band. (It can also be constructed with corresponding loop tape.)

The facial dressing is used for an array of procedures. It is designed to support and/or give compression to different areas of the face (head and neck) and provide support for one or more hot and/or cold pouches held against the face. By making minor adjustments with the band 20 and strap 30 it is ideal for the following:

| | |
|---|---|
| Antisnoring Support | Maxillofacial Surgery |
| Chin Augmentation | Oral Surgery |
| Compression Dressings | Otoplasty |
| Coronal Lift | Parotid Gland Surgery |
| Dental Extraction Surgery | Platysmal Neck Cont. |
| Facelift | Submandibular Lipectomy |
| Facial Liposuction | Submandibular Liposuction |
| Genioplasty | Submentoplasty |
| Hair Transplant | TMJ Arthroscopy |
| Mandibular Osteoplasty | Temporomandibular Joint |
| Mandibular Surgery | Surgery; | and thermal treatment associated with any of the above.

While the invention has been described with regards to specific embodiments, those skilled in the art will recognize that changes can be made in form and detail without departing from the spirit and scope of the invention.

I claim:

1. A medical treatment garment comprising:
   a pouch assembly including a container for holding a thermal reservoir which is covered on a first side with a hook tape covering; and
   a band being adapted to encircle a face (head or neck) in one of a plurality of various positions, wherein said hook tape covering is removably attachable to any location along said band; and a strap separate from said band, said strap having two ends, each of said ends being removably attachable with any location along said band, said strap connecting a set of any two points of said band around only one side of such an encircled face (head or neck).

2. A medical garment comprising:

a pouch assembly including a container for holding a thermal reservoir which is covered on a first side with a hook tape covering; and a band being adapted to encircle a face (head or neck) in one of a plurality of various positions, wherein said hook tape covering is removably attachable to any location along said band;

a first strap separate from said band, said first strap having two first strap ends, each of said first strap ends being removably attachable with any location along said band, said first strap connecting a set of any two points of said band around only a first side of such an encircled face (head or neck); and a second strap separate from said band, said second strap have two second strap ends, each of said second strap ends being removably attachable with any location along said band, said second strap connecting a set of any two points of said band around only a second side of such an encircled face (heard or neck).

* * * * *